(12) United States Patent
Gomez Zubicaray et al.

(10) Patent No.: US 10,557,799 B2
(45) Date of Patent: Feb. 11, 2020

(54) APPARATUS AND METHOD FOR THE INSPECTION OF CONTAINERS

(71) Applicants: Tech Pro Packag S.L., Amurrio (ES); Ingenet Automatizacion, S.L., Orozko (ES)

(72) Inventors: Unai Gomez Zubicaray, Laudio (ES); Jose Luis Pacho Pacho, Laudio (ES)

(73) Assignees: TECH PRO PACKAG S.L., Amurrio (ES); INGENET AUTOMATIZACION, S.L., Orozko (ES)

( * ) Notice: Subject to any disclaimer, the term of this patent is extended or adjusted under 35 U.S.C. 154(b) by 0 days.

(21) Appl. No.: 16/203,992

(22) Filed: Nov. 29, 2018

(65) Prior Publication Data

US 2019/0094152 A1 Mar. 28, 2019

Related U.S. Application Data

(63) Continuation of application No. PCT/ES2017/070367, filed on May 30, 2017.

(30) Foreign Application Priority Data

May 31, 2016 (EP) .................................... 16382248

(51) Int. Cl.
*G01N 21/00* (2006.01)
*G01N 21/90* (2006.01)
(Continued)

(52) U.S. Cl.
CPC ....... *G01N 21/909* (2013.01); *B21D 51/2638* (2013.01); *B21D 51/2692* (2013.01); *G01M 3/38* (2013.01); *G01N 21/894* (2013.01)

(58) Field of Classification Search
CPC ................ B07C 5/3408; G01N 21/909; G01N 21/9054; G01N 21/9036; G01N 21/90
(Continued)

(56) References Cited

U.S. PATENT DOCUMENTS 4,074,809 A * 2/1978 McMillin .............. B07C 5/3404
209/588
5,088,533 A 2/1992 Binder
(Continued)

FOREIGN PATENT DOCUMENTS

DE 10236951 A1 6/2004
EP 1531017 A1 5/2005
(Continued)

OTHER PUBLICATIONS

International Search Report and Written Opinion in corresponding International Application No. PCT/ES2017/070367, dated Sep. 19, 2017, 14 pages.
(Continued)

*Primary Examiner* — Md M Rahman
(74) *Attorney, Agent, or Firm* — Edell, Shaprio & Finnan, LLC

(57) ABSTRACT

According to one embodiment a necking machine is provided for containers with an open end. The necking machine may comprise a plurality of holding stations for containers and a plurality of tool stations contiguous and opposing the holding station. The tool stations being movable with respect to each other. The machine also includes an inspection device for containers that includes a light detector for detecting light in the interior of each container. The inspection device is attached to a tool station such that the inspection device shifts together with the tool station with respect to the container during the inspection of the container. Light communication of the light detector with the
(Continued)

interior of the container being maintained during the inspection.

22 Claims, 5 Drawing Sheets

(51) Int. Cl.
    *B21D 51/26*     (2006.01)
    *G01N 21/894*     (2006.01)
    *G01M 3/38*     (2006.01)

(58) Field of Classification Search
    USPC ........................................................ 356/240.1
    See application file for complete search history.

(56) References Cited

U.S. PATENT DOCUMENTS

| | | |
|---|---|---|
| 2009/0266131 A1 | 10/2009 | Dunwoody |
| 2012/0060578 A1 | 3/2012 | Weis |
| 2013/0208105 A1 | 8/2013 | Schmidt et al. |
| 2014/0253718 A1 | 9/2014 | Leitzen et al. |
| 2015/0192493 A1 | 7/2015 | Kouji et al. |
| 2015/0253260 A1 | 9/2015 | Kouji et al. |
| 2016/0045841 A1* | 2/2016 | Kaplan ................ B01J 19/0093 429/49 |
| 2017/0246399 A1* | 8/2017 | Forlani ............. A61M 5/31568 |

FOREIGN PATENT DOCUMENTS

| | | |
|---|---|---|
| EP | 2778103 A1 | 9/2014 |
| JP | H0862154 | 3/1996 |

OTHER PUBLICATIONS

Extended European Search Report in corresponding EP Application No. 16382248.9, dated Jan. 4, 2017, 7 pages.

* cited by examiner

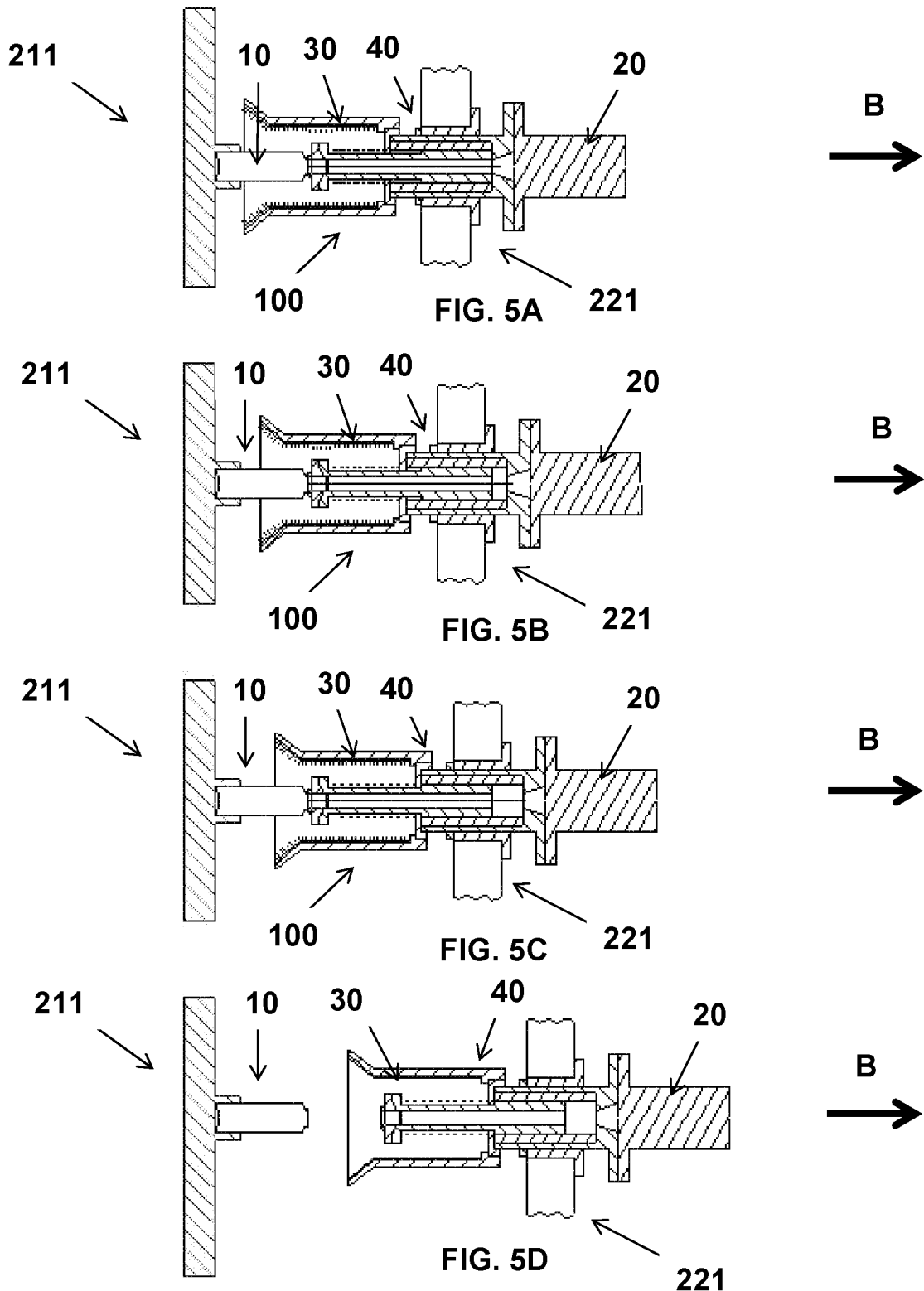

APPARATUS AND METHOD FOR THE INSPECTION OF CONTAINERS

CROSS-REFERENCE TO RELATED APPLICATIONS

This application relates to and claims the benefit and priority to International Application No. PCT/ES2017/070367, filed May 30, 2017, which relates to and claims the benefit and priority to European Application No. EP16382248.9 filed May 31, 2016.

TECHNICAL FIELD

The present invention relates to necking machines for containers, particularly metal containers and to methods for the inspection of containers implemented with the machines.

BACKGROUND

Apparatus or machines that are part of the general automated metal container forming process, such as aluminum containers for beverages or hygiene products, for example, are known. The apparatus within the process performing from the process of transforming the raw material into a container, for example a cylindrical-shaped container, the process of cutting the container to a specific length, washing the cut container, varnishing the interior, decorating the outer side surface of the container, enameling the outer surface of the container, deforming the side surface, and inspecting the containers to control possible defects arising during the process.

Some of the most common defects in containers are small openings and cracks on the side surface of the containers, as well as small dents and cracks on the edge of the containers. Inspection apparatus which perform only this control operation continuously, are commonly used and are arranged after the container side surface deformation process. Machines performing container side deformation, and inspection operations on the containers are also known. Problems during the subsequent filling of the containers are thereby prevented.

Inspection is performed by irradiating light from a light source on the outer surface of the containers, and by arranging a light detector in light communication with the interior of the containers, through an open end of the containers. Light communication is performed in an environment that is isolated from external light, such that if the inspected container has a small opening on its surface, for example, the external light will enter the container and the light detector will detect it.

US2015/0192493A1 discloses a machine for the inspection of containers which only performs inspection operations, comprising a holding table with a plurality of holding stations for holding the containers, a respective inspection table contiguous to and opposite the holding table, with an inspection station, and a light source irradiating the outer surface of each container that is inspected with light. The holding table receives the containers in the holding stations and shifts them in a rotating and indexed manner in defined positions. The holding table comprises a holding plate with a plurality of holding stations individually holding the containers, a support plate, opposite the holding plate, with a plurality of openings opposite the holding stations of the holding plate, and pushing members shifting the containers towards the holding stations when they enter the holding table, the open ends of the containers being supported in the openings of the support plate.

The inspection table is stationary and comprises an inspection station with an inspection device having a light detector attached to the inspection station with support means, the support means comprising an outer plate comprising an opening that is in light communication with the light detector. The support plate of the holding table is supported in a sliding and rotating manner on the outer plate of the inspection station, light communication between the light detector and each container taking place in an indexed manner.

US2013/0208105A1 discloses a machine for the inspection of containers that is a necking machine that forms necks and deforms the container side surface. The necking machine comprises a holding table with a holding plate comprising a plurality of holding stations for holding the containers by their base, shifting the containers in a rotating and indexed manner in defined positions. The machine also comprises a respective tool table contiguous to and opposite the holding table, with a plurality of positions comprising tool stations, and a position comprising an inspection station with an inspection device.

The inspection device comprises a stationary support plate in which a jacket tube is supported, a camera and a light source being arranged in the jacket tube. The inspection device also comprises a support element parallel to the support plate that is movable with respect to the plate. A retaining tube arranged concentrically with respect to the jacket tube on the outer portion is supported in the support element. This retaining tube has optical elements in the inner portion of its free end. At the same time, the axis of the assembly formed by the jacket tube and the retaining tube coincides with the axis of the container that is going to be inspected, such that when the support element shifts towards the holding plate, part of the container to be inspected is surrounded by the retaining tube and opposite the jacket tube. When light is irradiated from the light source, the optical elements forward the reflected image of the container to the camera, the camera recording the possible defects the container may have.

SUMMARY OF THE DISCLOSURE

One aspect of the disclosure relates to a necking machine for containers with an open end to be conformed, comprising a plurality of holding stations for containers and a plurality of tool stations contiguous and opposite, the holding stations and the tool stations being movable with respect to each other, the machine also comprising an inspection device for containers comprising a light detector for detecting light in the interior of each container. The inspection device is attached to a tool station, such that the inspection device shifts together with the tool station with respect to the container during the inspection of each container, light communication of the light detector with the interior of the container being maintained during the inspection. In the event of any holes or cracks in the container, the exterior light, which may be ambient light or light irradiated by a light source, reaches the interior of the container and is detected by the light detector.

The inspection device comprises a stop with an opening communicating the light detector with the exterior, the stop shifting only to the open end of the container to be inspected, and the inspection of the container being carried out during the time in which the stop is in contact with the open end of the container.

Another aspect of the invention relates to a method for the inspection of containers that is implemented with a machine such as the one defined above.

In the necking machines of the prior art, the light detector performing inspection of the container is stationary and it is the container that is brought closer to the light detector, or it comprises means that bring the containers closer and allow reflecting images to means that allow capturing the images.

In the necking machine disclosed herein, the light detector shifts towards the container, and it is during that shifting when the container is inspected by means of the light detector. In this way, the inspection of the containers is integrated into the process of forming necks in the necking machine itself, with the savings in costs this entails, and is also integrated in such a way that it is not necessary to transform the necking machine, it is sufficient to couple the inspection device to one of the tool stations of the necking machine. The inspection is performed during the relative shifting of the holding table comprising the holding stations for holding the containers, with respect to the tool table comprising the tool station with the inspection device, and the tool table does not require incorporating support elements that shift with respect to the stationary support plate itself that supports the inspection device.

These and other advantages and features will become evident in view of the drawings and detailed description.

BRIEF DESCRIPTION OF THE DRAWINGS

FIGS. 5A-D illustrate a method of inspection as the tool table shifts in a direction B from the forward position to the back position.

DETAILED DESCRIPTION

The manufacture of a metal container and the transformation thereof, particularly an aluminum container for a beverage or hygiene product, for example, requires a process involving different machines. The machines are automatically linked together, the transformation process being a high-speed process.

One example of a transformation process of an aluminum container the side surface of which is deformed and decorated with a design, comprises the following machines:

Extruder: where aluminum sheet is transformed into a cylinder as a container.
Cutting machine: where the cylinder is cut to a specific length.
Washer: where greases and oils are washed out of the container.
Internal varnishing machine: where the container is internally coated with a varnish.
Lithographic unit: formed by three machines in this process example:
Varnishing machine: prepares the exterior of the container, coating it prior to printing the design.
Printer: prints the design and an identification code on the container digitally or by means of an off-set system.
Enameling machine: externally coats the container to protect the printing.
Necking or neck forming machine: where the container is deformed and completely finished.

The process is completed with industrial furnaces and accumulators.

The starting raw material may have some type of defect, or some type of defect may occur in the process. These defects can be, for example, small openings and cracks on the side surface of the containers, as well as small dents and cracks on the edge of the containers. Container inspection apparatus which perform only this control operation continuously are commonly used and are arranged after the necking or neck forming machine. This lengthens the process and increases the costs as a result of this lengthening, plus the actual cost of the inspection apparatus and its maintenance.

Figure 3:
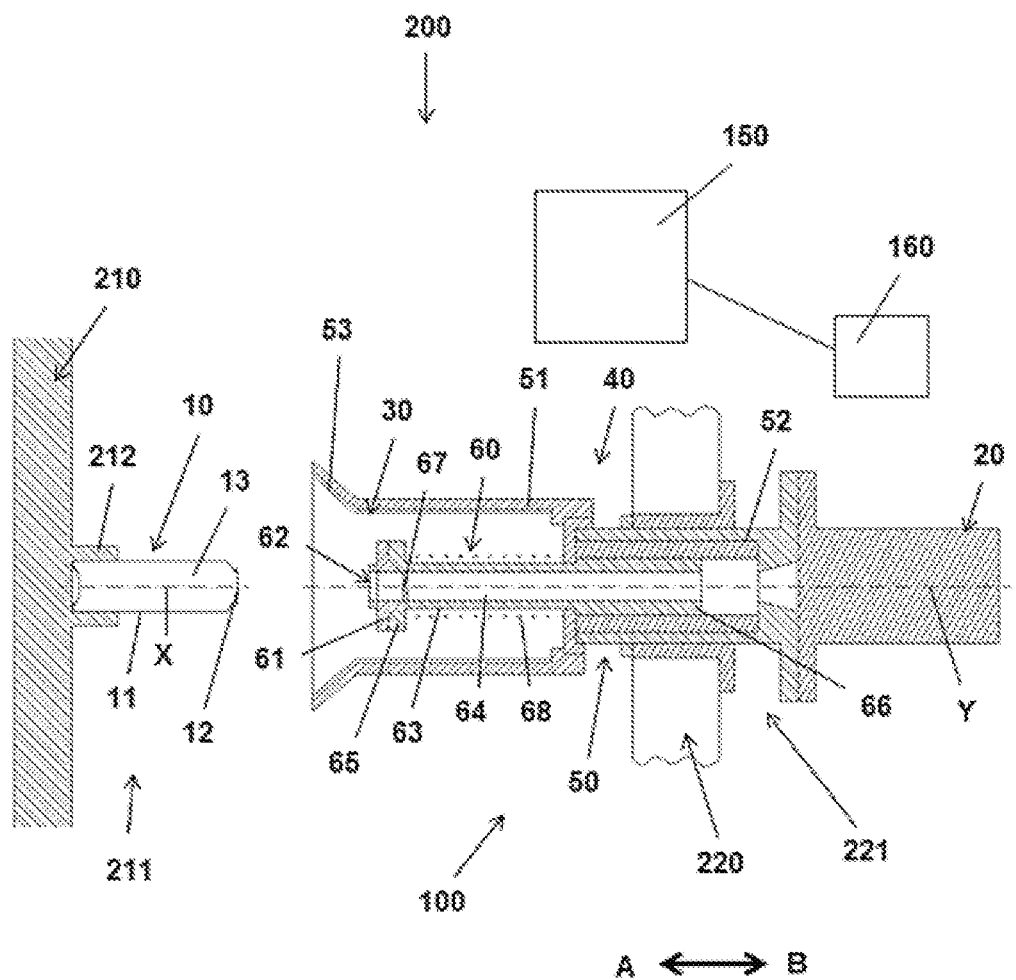
FIG. 3 shows a partial cross-section view of an embodiment of an inspection device.
Figure 4A:
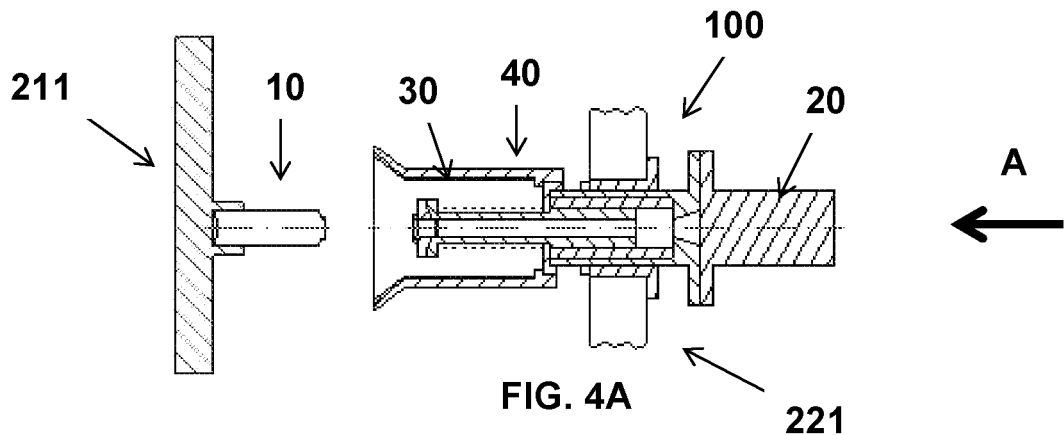
FIGS. 4A-D illustrate a method of inspection as the tool table shifts in a direction A from a back position to a forward position.
Figure 4B:
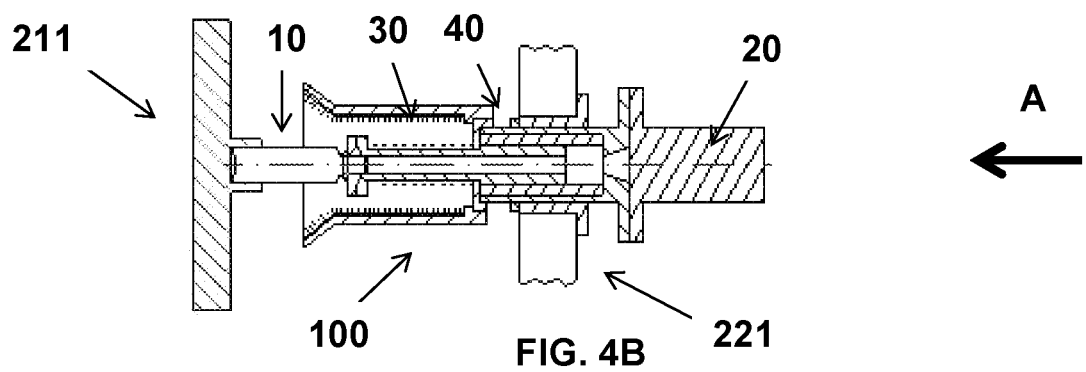
Figure 4C:
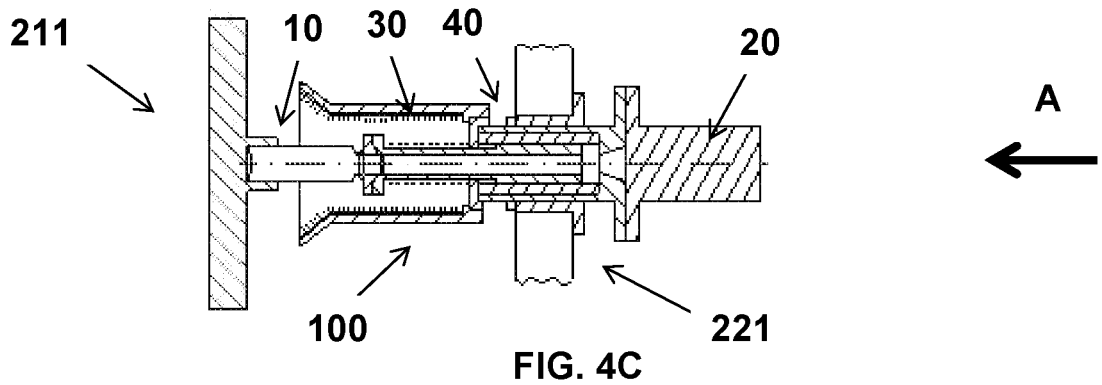
Figure 4D:
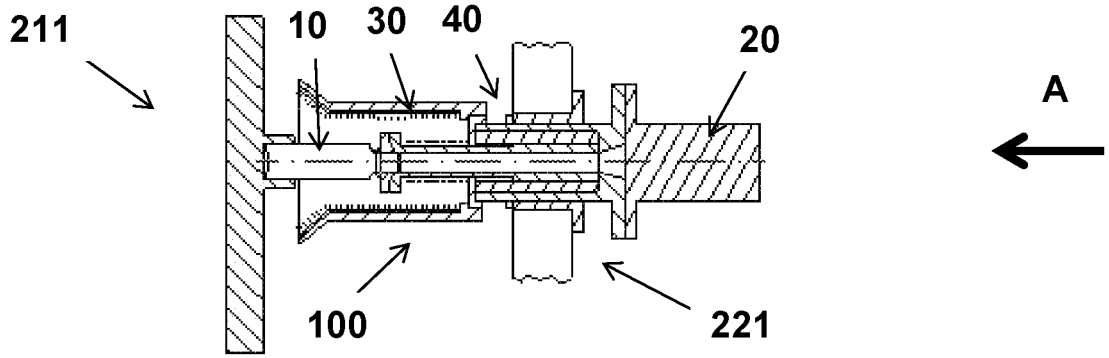

According to one embodiment the machine 200 is a necking machine, where the container 10 undergoes deformation on the side surface, and it is where the neck of the container 10 is formed in its open end 12. To that end, as shown in FIG. 3 in a partial cross-section view of one embodiment of the machine 200, the machine 200 comprises a rotating, vertically oriented holding table 210. The holding table 210 receives containers 10 from the preceding machine in the transformation process by means of a feed line (not shown in the drawings).

The holding table 210 has a rotational movement around a horizontal axis, in an indexed manner in defined positions. The holding table 210 comprises a plurality of holding stations 211 arranged along the periphery thereof, the number of holding stations normally being comprised between 16 and 50, there often being 40. As the containers 10 move forward in the transformation process, they reach the holding table 210 by means of the feed line in a sequenced manner, the containers 10 being fed to the holding table 210, and each container 10 being arranged in a holding station 211. Each container 10 is held in each holding station 211 fixed at its base, the base of the container 10 being located in a position opposite the open end 12 or open end for the opening of the container 10, by means of a holding clamp 212.

The machine 200 in this embodiment comprises a vertically oriented tool table 220. The tool table 220 experiences translational movement A towards the holding table 210 from a back position to a forward position, and translational movement B from the forward position to the back position. After each indexed rotational movement of the holding table 210, the tool table 220 moves forward with the translational movement A and moves back with the translational movement B, before the following rotational movement of the holding table 210. The tool table 220 comprises a plurality of tool stations 221 arranged along the periphery thereof, the number of tool stations being equivalent to the number of holding stations, being able to vary, for example, by a number of three lower units. Each tool station 221 is located in a position contiguous to and opposite a holding station 211 during deformation of the container 10, the deformation taking place during the translational movement A of the tool table 220.

Figure 1A:
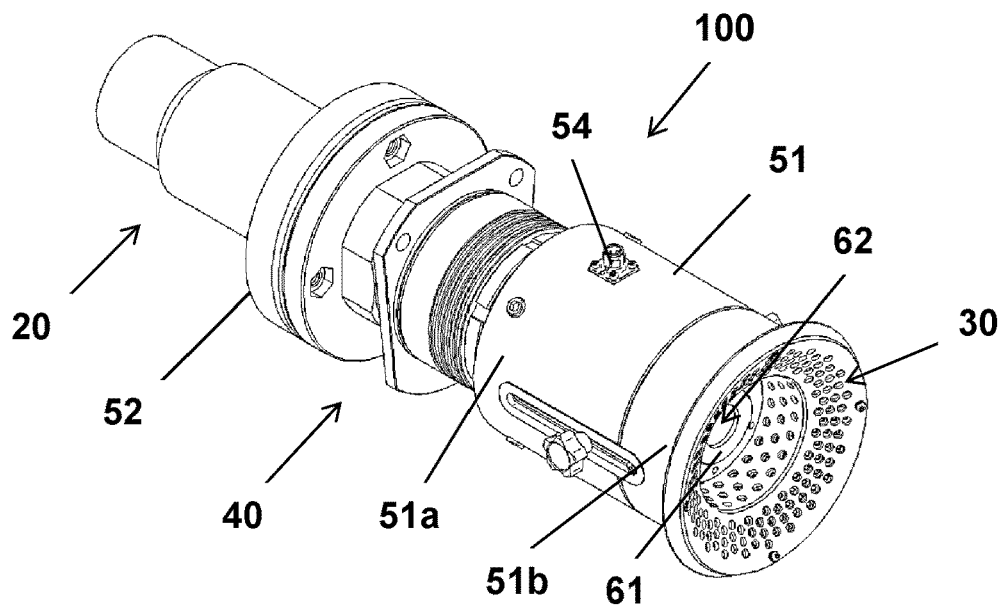
FIG. 1A shows a perspective view of a first embodiment of an inspection device.
Figure 2A:
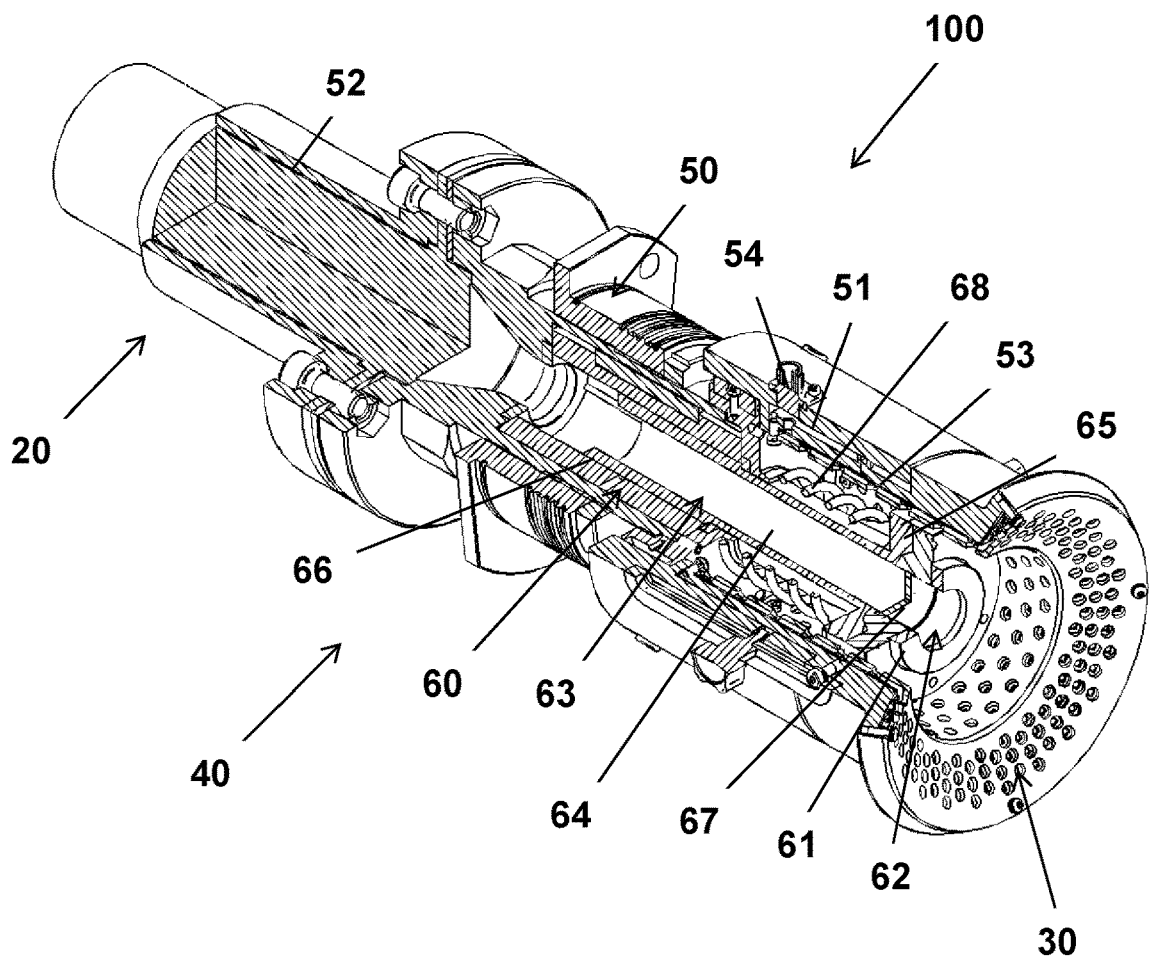
FIG. 2A shows a perspective cross-section view of the inspection device of FIG. 1A.
Figure 2B:
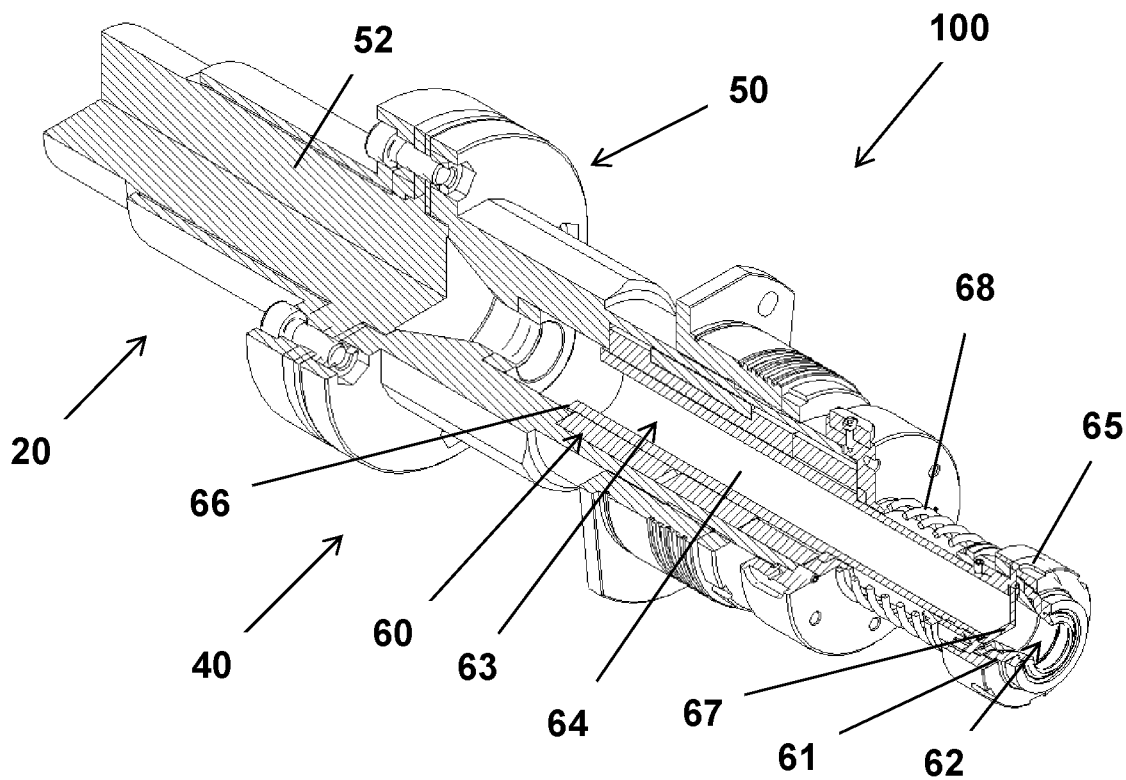
FIG. 2B shows a perspective cross-section view of the inspection device of FIG. 1B.

The machine 200 comprises in one of the tool stations 221 an inspection device 100 for inspecting the containers 10, attached to the tool station 221 as if it were a tool for deforming the side surface or forming the neck of the container 10. The arrangement of the inspection device 100 in the tool table 220 is preferably the last position or one of the last positions, a tool for eliminating greases and dirt in the container 10 taking the last position in this case. FIGS. 1A and 2B show a perspective view and a perspective cross-section view, respectively, of a first embodiment of the inspection device 100 of the machine 200.

The inspection device 100 comprises a light detector 20 for detecting light in the interior 13 of the container 10, support means 40 attaching the inspection device 100 to the tool station 221, and supporting the light detector 20, allowing light communication of the light detector 20 with the interior 13 of the container 10 when the container 10 is inspected, as will be explained below, and a light source 30 irradiating an outer surface 11 of the container 10 with light. The light detector 20 that is attached to the inspection device 100, the inspection device 100 that is attached to the tool station 221, and the tool station 221 that is arranged in the tool table 220, the light detector 20 shifts with the translational movement of the tool table 220 in directions A and B, with respect to the container 10 that is arranged in the holding station 211 of the respective holding table 210, during the inspection of the container 10, light communication of the light detector 20 with the interior 13 of the container 10 being maintained.

Light communication is understood as the union formed between different means or elements that allows the passage of light from all wavelength ranges, e.g., from ultraviolet light to the infrared light, preferably being white light.

The inspection device 100 has a substantially tubular or cylindrical general shape, comprising an axial axis X running through it. The container 10 also generally has a substantially cylindrical shape. Upon rotating the holding table 210, when the container 10 to be inspected is arranged opposite the tool station 221, where the inspection device 100 is located, the axis X of the inspection device 100 coincides with the axis of the container 10. Therefore, when the tool table 220 shifts in translational movement in directions A and B, the light detector 20 arranged in the inspection device 100 shifts in the direction of the axis of the inspected container 10.

In this first embodiment of the machine 200, the support means 40 of the inspection device 100 comprise a support 50 supporting the light detector 20 and the light source 30, which is arranged in the inspection device 100 in this first embodiment of the inspection device 100. The support means 40 also comprise shifting means 60 that is attached to the support 50 in a sliding manner. The shifting means 60 allows light communication between the interior 13 of the container 10 and the light detector 20.

The support 50 in this first embodiment of the inspection device 100 comprises a first support 51 and a second support 52 which have a substantially cylindrical shape and are tubular, so they are internally hollow. The first support 51 and the second support 52 are attached with attachment means known in the prior art, such as by means of threading, for example. The first support 51 is arranged in the inspection device 100 closest to the opposing container 10, and then, moving away from the container 10, the second support 52 is attached to the first support 51. The first support 51 has a substantially cylindrical shape in the area closest to the attachment with the second support 52 and transforms into a frustoconical shape moving away from the attachment with the second support 52, the diameter thereof increasing, and being open at its end close to the opposing container 10, the open end of the first support 51 allowing the entry of the container 10.

The first support 51 has an inner surface 53 to which the light source 30 is attached. The light source 30 is formed, in this embodiment of the inspection device 100, by two aluminum plates, one cylindrical plate and another conical plate, with a plurality of cavities where 24 Vdc LED blue lights are arranged, distributed over the entire surface of the plates. The plates are fixed to the inner surface 53 of the first support 51, irradiating light into the cylindrical portion, and the frustoconical portion allowing irradiating light also out of the first support 51, in the direction of the holding station 211 where the container 10 to be inspected is located. The light intensity of the light source 30 can be varied, being increased if required.

When the tool table 220 shifts during translational movement in direction A towards the holding table 210 from the back position to the forward position, depending on its length, the container 10 can be arranged completely or partially inside the first support 51 when the tool table is located in its forward position. During translation in direction A to the forward position, and in direction B to the back position, the container 10 is introduced in and comes out of the inside of the first support 51, respectively.

The light detector 20 is attached at the opposite end of the inspection device 100, attached to one end of the second support 52, farther away from the first support 51, the light detector 20 being in light communication with the hollow interior of the second support 52, which is in turn in light communication with the hollow interior of the first support 51. The light detector 20 comprises in this embodiment of the machine 200 a highly sensitive optical sensor, the sensitivity being configurable, with a photomultiplier that allows detecting small holes at a high exposure speed and with great precision, the photomultiplier being excited with very little light and sending an electric signal when it is excited. The sensor could detect small holes of up to 10 µm on the outer surface 11 of the container 10, which allow light beams to enter the interior 13 of the container 10, but in practice and with the inspection device 100 mounted and operating in the machine 200, it allows detecting holes of 100 µm, which is less than the 200 µm safety measurements allowed by manufacturers of containers of this type. The light detector 20 also comprises a power unit that receives the electrical signal from the photomultiplier and sends it to a control unit 160 of the light detector 20 for the corresponding processing thereof.

The shifting means 60 that is attached in a sliding manner to the support 50 comprise a movable support 63 attached in a sliding manner to the second support 52 of the support 50, a stop 61 attached to the movable support 63, and elastic means 68 that is supported between the movable support 63 and the second support 52. Therefore, the movable support 63 is arranged on the axis X of the inspection device 100, and in this embodiment it is arranged inside the inspection device 100 between the open end of the first support 51 and the end of the second support 52 that is attached to the light detector 20.

The movable support 63 is a tubular part comprising a hollow inner conduit 64, with a first end 65 with a diameter greater than that of the central body of the movable support 63, and a second end 66. The stop 61 is also a tubular part with an opening 62 with an inner diameter similar to the inner diameter of the inner conduit 64 of the movable support 63, the stop 61 being attached to the first end 65 and the opening 62 and the inner conduit 64 being in light communication. Likewise, the second end 66 of the movable support 63 is in light communication with the light detector 20, so there is light communication from the light detector 20 to the opening 62 of the stop 61. The attachment of the first end 65 of the movable support 63 to the stop 61 of the shifting means 60 is a pivoting attachment. Therefore, the attachment is performed in this embodiment of the inspection device 100 by placing a joint between the first end 65 and the stop 61, such that the stop 61 is arranged in a floating, and therefore pivoting, manner on the first end 65 of the movable support 63. This type of attachment allows absorbing alignment differences between the movable support 63 of the shifting means 60 and the axis of the container 10 which may arise due to problems in anchoring the holding or due to shape-related problems of the container 10.

To obtain a sliding attachment between the movable support 63 and the second support 52, the movable support 63 is formed with two parts, a fixed tube arranged at the end of the movable support 63 and comprising the second end 66, which is close to the light detector 20, and a mobile tube which can slide by means of a bearing inside the fixed tube, and the end of which farthest away from the light detector 20 is the first end 65. There is a hollow space between the second end 66 and the light detector 20 in which there is arranged a conical part that allows light communication between the light detector 20 and the hollow conduit 64 of the movable support 63, with a joint protecting against impacts on the side of the second end 66. To prevent problems with dirt in the light detector 20 which may come from the exterior through the shifting means 60, the shifting means 60 comprises a transparent plate 67 closing the inner conduit 64 of the movable support 63, and allowing the passage of light.

When the tool table 220 shifts during translational movement in direction A towards the holding table 210, from the back position to the forward position, the inspection device 100 is brought closer to the container 10 and reaches a point while shifting in which the open end 12 of the container 10 is supported on the stop 61 of the shifting means 60. Due to the forward movement of the inspection device 100 to the forward position, the open end 12 of the container 10 pushes the stop 61 and this stop 61 transmits the pushing to the movable support 63, such that the mobile tube of the movable support 63 slides inside the fixed tube. When the container 10 reaches the forward position, depending on its length it is located completely or partially inside the first support 51. The joint protecting against impacts allows absorbing possible impacts therein caused by supporting the container on the stop 61, and during its subsequent translational movement inside the inspection device, which could otherwise be transmitted to the light detector 20.

The elastic means 68 of the shifting means 60 is supported between the first end 65 and the second support 52, such that when the open end 12 of the container 10 pushes the stop 61, the elastic means is compressed until the tool table 220 reaches the forward position in translational direction A. When the tool table 220 moves back towards the back position in translational direction B, the elastic means 68 is decompressed and allow the return of the shifting means 60 to its initial position, contact between the stop 61 and the open end 12 of the container 10 being maintained during the inspection of the container 10, and the open end 12 of the container 10 being disconnected from the stop 61 of the shifting means 60 before the tool table 220 reaches the back position. During the time of the shifting cycle in translational directions A and B in which the open end 12 of the container 10 is in contact with the stop 61, light communication is maintained between the interior 13 of the container 10 and the light detector 20. To that end, the stop 61 has in the area where the open end 12 of the container 10 is supported, a profile with curved shapes preventing exterior light from entering the hollow conduit 64 of the movable support 63 and reaching the light detector 20, thereby preventing problems in the inspection of the containers 10, and even preventing damage to the light detector 20. To prevent the wearing of the stop 61 due to its continued use during inspection operations on containers 10, the stop 61 is preferably made of metal instead of another more elastic material but with a higher tendency to wear, and therefore requiring being replaced more often.

The machine 200 comprises control means 150 which can be a PLC, for example, which controls and governs rotational movement of the holding table 210 and translational movement of the tool table 220 during movement A towards the holding table 210 from a back position to a forward position, and during movement B from the forward position to the back position. The function of this PLC is to furthermore synchronize the different operations and actions that must be carried out during the entire process of deforming the container 10 in the machine 200.

The control of the PLC over the indexed position of each holding station 211 incorporating a container 10, and the control of the tool table 220, and specifically the control of the tool station 221 where the inspection device 100 is arranged, can be done by means of electrical signals coordinating the position of each holding station 211 with a container 10 and the relative position of each tool station 221, and therefore of the tool station 221 where the inspection device 100 is located, the PLC also receiving inspection signals from the control unit 160 of the light detector 20. Control can also be performed by means of an encoder (not depicted in the drawings) mounted in the rotating motor of the holding table 210, the encoder being connected to the PLC, and the encoder indicating the angle at which the holding table 210 is rotated. The PLC therefore precisely knows the position of each holding station 211, and when the container to be inspected reaches the position opposite the tool station 221 of the inspection device 100, it controls translational movements A and B of the tool table 220.

Control of the translational movement of the tool table 220, and specifically control of the movement of the inspection device 100 in the tool station 221 in which it is arranged, is performed considering that the complete cycle of movement A+B is 360°, each movement A and B corresponding to 180°, respectively. In this embodiment of the machine 200, when the tool table 220 is to be moved during translational movement A from the back position to the forward position, when the position of the tool table 220, and therefore of the inspection device 100, has been subjected to translational movement corresponding to 140°, the open end 12 of the container 10 comes into contact with the stop 61 of the shifting means 60 of the inspection device 100. The inspection device 100 continues shifting to the position corresponding to 180°, and the open end 12 continues pushing and being in contact with the stop 61, which moves back compressing the elastic means 68.

When the tool table 220 is to be moved during translational movement B from the forward position to the back position, the open end 12 of the container 10 continues to be in contact with the stop 61 due to the decompression movement of the elastic means 68. When translation corresponding to 220° from the start of translational movement A, and 40° from the start of translational movement B has been performed, the open end 12 of the container 10 is no longer in contact with the stop 61 of the shifting means 60 of the inspection device 100. The inspection device 100 continues shifting to the back position corresponding to 360°.

The path of the translational movement between 140° and 220° corresponding to the position in which the open end 12 of the container 10 is in contact with the stop 61 of the inspection device 100 allows performing inspection of the container 10, activating the light source 30, and the light detector 20 detecting whether or not there is light in the interior 13 of the container 10. This path can vary depending on the length of the container 10, for example. To adjust the translational path corresponding to the inspection time to a variation in the length of the containers 10, one alternative is to define a path of the translational movement other than 140° and 220°, and adjusted to the length of the container 10 and to the length of outer surface 11 of the container 10 to be inspected, by calculating the segment of the outer surface 11 that is to be inside the first support 51 of the support means 40. The portion of the light source 30 comprised in the frustoconical portion allows irradiating the outer surface 11 of the container 10 that is not introduced inside the first support 51 with light.

Another alternative is to adjust the length of the first support 51 to the length of the container 10, in this case the first support 51 comprising two separate portions 51*a* and 51*b* attached by attachment means 54 (not shown in the drawings), for example a screw. For these cases, and given that the total length of the first support 51 can increase, the movable support 63 of the inspection device 100 comprises a bearing having a larger path that allows the mobile tube to shift a greater distance with respect to the fixed tube.

Figure 1B:
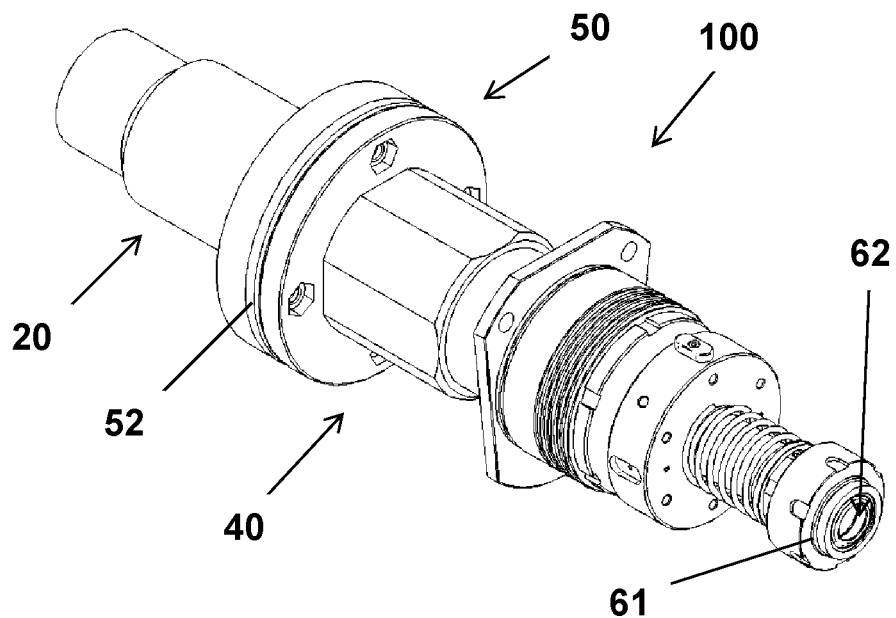
FIG. 1B shows a perspective view of a second embodiment of an inspection device.

FIG. 1B shows a perspective view of a second embodiment of an inspection device 100 of the machine 200 for the inspection of containers 10. FIG. 2B shows a perspective cross-section view of the inspection device 100 of FIG. 1B.

This second embodiment of the inspection device 100 comprises the same elements as the first embodiment, except the first support 51 of the support 50, and therefore does not comprise the inner surface 53 of the first support 51 either, nor the light source 30 attached to the inner surface 53. Therefore, in this second embodiment there is no light source arranged in the inspection device 100. In these circumstances, the light incident on the outer surface 11 of the container 10 to be inspected may be the ambient light itself, or there may be a specific light source arranged for example in the machine structure 200 itself. The method for the inspection of containers 10 is implemented, for example, with a machine 200 suitable according to the described embodiments. FIGS. 4A-D and FIGS. 5A-D show the steps of an embodiment of a method for the inspection of containers 10 with the machine 200 of the first embodiment. The method comprises:

a holding step for holding the container 10, the container 10 being held in a holding station 211 of the holding table 210 of the machine 200, the tool table 210 moving in a rotational movement around a horizontal axis in an indexed manner in defined positions, the control means 150 controlling the position of a container 10 to be inspected opposite a tool station 221 where the inspection device 100 is arranged, and a shifting step for shifting the tool station 221 comprising the inspection device 100 with respect to the holding station 210 where the container 10 to be inspected is held, the shifting step comprising translational movements A and B, shifting from the back position to the forward position and from the forward position to the back position, respectively. The shifting step comprising along the path thereof the phases of:

forward movement of the tool station $220_i$ during translational movement A with shifting comprised between 0° and 180°, backward movement of the tool station $220_i$ during translational movement B with shifting comprised between 180° and 360°, and inspection of the container 10 during shifting of the inspection device 100, the inspection being performed during the forward movement and backward movement phases of the tool table 220, the inspection phase starting when the stop 61 of the shifting means 60 of the support means 40 comes into contact with the open end 12 of the container 10 at 140° of translational movement A, and ends when the stop 61 is no longer in contact with the open end 12 of the container 10 at 220° of translational movement B. The inspection phase in turn comprises the following steps:

Step 1: at 141° of the shifting path, the control unit 160 of the light detector 20 first checks to see if there is container 10 to be inspected, checking with the light detector 20 if there is darkness in the light communication theoretically established between the interior 13 of the container 10 and the light detector 20. If there is darkness, there is a container 10 to be inspected and it is correctly arranged.

Step 2: at 142°, after having checked that there is a container 10 to be inspected, the control unit 160 optionally activates the light source 30 irradiating the outer surface 11 of the container 10 (It will do so in case there is a light source 30, as occurs in the first embodiment).

Step 3: if the container 10 has any defect, for example a small hole, that allows the passage of light to its interior 13, and the light detector 20 detects it, the light sensor 20 sends the electrical signal to the control unit 160 indicating that the container 10 is defective, and the control unit 160 deactivates the light source 30 at 150° of the shifting path to protect the light detector 30. If the container 10 has no defects allowing the passage of light to its interior 13, the light detector 20 and the light source 30 remain active along the entire inspection path between 140° and 220°, the light source 30 being deactivated at 219° of the shifting path. In the event of a defective container 10 and in the event of a correct container 10, the control unit 160 sends the corresponding signals to the control means 150.

The control means 150 memorize the positions of the containers 10 together with the result of their inspection, such that upon reaching a container ejection unit normally located after the machine 200 in a feed line, the control means 150 activate the ejection unit, and defective containers are removed from the line.

The following clauses disclose in an unlimited way additional implementations, with each clause representing an implementation.

Clause 1: A necking machine for containers 10 with an open end 12 to be conformed, comprising a plurality of holding stations 211 for containers 10 and a plurality of tool stations 221 contiguous and opposite, the holding stations 211 and the tool stations 221 being movable with respect to each other, the machine 200 also comprising an inspection device 100 for containers 10 comprising a light detector 20 for detecting light in the interior 13 of each container 10, so that, in the event of any holes or cracks in the container 10, the exterior light, which may be ambient light or light irradiated by a light source 30, reaches the interior of the container 10 and is detected by the light detector 20, the inspection device 100 is attached to a tool station 221, such that the inspection device 100 shifts together with the tool station 221 with respect to the container 10 during the inspection of each container 10, light communication of the light detector 20 with the interior 13 of the container 10 being maintained during the inspection, wherein the inspection device 100 comprises a stop 61 with an opening 62 communicating the light detector 20 with the exterior, the stop 61 shifting only to the open end 12 of the container 10 to be inspected, and the inspection of the container 10 being carried out during the time in which the stop 61 is in contact with the open end 12 of the container 10.

Clause 2: The machine according to clause 1, wherein the inspection device 100 comprises a support 50 fixing the light detector 20 to the tool station 221, and shifting means 60 incorporating the stop 61, the shifting means 60 being attached to the support 50 in a sliding manner.

Clause 3: The machine according to clause 2, wherein the shifting means 60 comprise elastic means 68 that are supported between the shifting means 60 and the support 50, the elastic means 68 maintaining contact between the stop 61 and the open end 12 of the container 10 during the inspection of the container 10.

Clause 4: The machine according to clause 2 or 3, wherein the shifting means 60 comprise a movable support 63 attached to the support 50, the movable support 63 comprising a hollow inner conduit 64 between a first end 65 and a second end 66 of the movable support 63, the first end 65 being attached to the stop 61, with the opening 62 and the inner conduit 64 in light communication, and the second end 66 being in light communication with the light detector 20.

Clause 5: The machine according to clause 4, wherein the attachment of the first end 65 of the movable support 63 with the stop 61 of the shifting means 60 is a pivoting attachment, that allows absorbing the alignment differences between the movable support 63 and the axis of the container 10.

Clause 6: The machine according to any of clauses 2 to 5, wherein the inspection device 100 for containers 10 comprises a light source 30 for irradiating an outer surface 11 of the container 10.

Clause 7: The machine according to claim 6, wherein the support 50 comprises a first support 51, the light source 30 being attached to the first support 51, and a second support 52 of the light detector 20, the first support 51 and the second support 52 being attached to one another, at least one portion of the first support 51 at least partially surrounding the container 10 in the shifting movement of the light detector 20.

Clause 8: The machine according to clause 7, wherein the first support 51 is a hollow part, being at least partially cylindrical-shaped, the light source 30 being distributed over the inner surface 53 of the first support 51, and the shifting means 60 being arranged on the axis of the first support 51.

Clause 9: A method for the inspection of containers 10, implemented with a machine 200 according to any of the preceding claims, characterized in that it comprises:

a holding step for holding the container 10 in a holding station 211 of the machine 200, and a shifting step for shifting the tool station 221 comprising the inspection device 100, with respect to the holding station 211, the shifting step comprising an inspection phase for inspecting the container 10 in the shifting of the inspection device 100, wherein the shifting step comprises a forward movement phase for moving the tool station 221 from a first position to a second position, and a backward movement phase for moving from the second position to the first position, the inspection phase for inspecting the container 10 being performed during the forward movement and/or backward movement phases of the tool station 221.

Clause 10: The method according to clause 9, wherein the inspection phase for inspecting the container 10 starts when the inspection device 100 comes into contact with the container 10, and ends when the inspection device 100 is no longer in contact with the container 10.

Clause 11: The method according to clause 10, wherein a light source 30 is activated when the inspection device comes into contact with the container 10, and is deactivated before the inspection device 100 is no longer in contact with the container 10.

Clause 12: The method according to clause 11, wherein the light source 30 is deactivated when the light detector 20 detects light in the interior 13 of the container 10.

Clause 13: The method according to clause 11 or 12, wherein in the inspection phase the presence of container 10 in the holding station 210 is checked before activating the light source 30.

What is claimed is:

1. An assembly comprising:
   an inspection apparatus for detecting holes or cracks in a container that possesses an interior and an open end, the inspection apparatus comprising:
   a light detector for detecting light in the interior of the container;
   a movable support having a first end, a second end and an inner through conduit extending between and through the first and second ends, the through conduit configured to communicate light received at the first end towards the light detector, the movable support movable between a first axial position and a second axial position, in the second axial position the second end of the movable support is located nearer the light detector than when the movable support is in the first axial position;
   an elastic member that acts on the movable support to continuously urge the movable support towards the first axial position; and
   a stop with an inner through opening located on the first end of the moveable support, the stop configured to contact the open end of the container in a manner that prevents light from entering the interior of the container through the open end of the container.

2. The assembly according to claim 1, further comprising a position detector and a controller, the position detector being configured to determine when the stop is in contact with the open end of the container, the controller configured to receive signals from the position detector and to activate the light detector only upon the stop being in contact with the open end of the container.

3. The assembly according to claim 1, further comprising a holding station configured to hold the container and a tool station located opposite the holding station, the holding station and the tool station being movable with respect to one another, the inspection apparatus being attached to the tool station and movable with the tool station, the tool station movable in a forward direction toward the holding station and in a rearward direction away from the holding station.

4. The assembly according to claim 3, wherein the stop is configured to make contact with the open end of the container during a movement of the tool station in the forward direction.

5. The assembly according to claim 4, wherein the stop is configured to make contact with the open end of the container during only a part of the time in which the tool station moves in the forward direction.

6. The assembly according to claim 3, wherein the stop is configured to make contact with the open end of the container during a movement of the tool station in the forward direction and the rearward direction.

7. The assembly according to claim 6, wherein the stop is configured to make contact with the open end of the container during only a part of the time in which the tool station moves in the forward direction, and during only a part of the time in which the tool station moves in the rearward direction.

8. The assembly according to claim 3, wherein the inspection device includes a support that fixes the light detector to the tool station, the movable support being attached to the support in a sliding manner.

9. The assembly according to claim 8, wherein the elastic member is supported between the moveable support and the support, the elastic member configured to cause the stop to be pushed against the open end of the container during an inspection of the container.

10. The assembly according to claim 9, wherein the inspection assembly includes a light source for irradiating an outer surface of the container, the support comprising a first support and a second support that are attached to one another, the light source being attached to the first support, the light detector being attached to the second support, at least a portion of the first support is configured to at least partially surround the container during a movement of the tool station in the forward and rearward directions.

11. The assembly according to claim 10, wherein the first support is a hollow part, the light source being distributed over an inner surface of the first support, and the moveable support being arranged about an axis of the first support.

12. The assembly according to claim 3, wherein the tool station and holding station are a part of a necking machine.

13. The assembly according to claim 1, wherein the stop is supported on the first end of the movable support by a pivoting attachment that allows absorbing the alignment differences between the movable support and the container.

14. The assembly according to claim 1, wherein the inspection device includes a light source for irradiating an outer surface of the container.

15. A method for detecting holes or cracks in a container that possesses an interior and an open end, the method comprising:
holding the container in a holding station;
providing an inspection apparatus that is moveable in a forward movement direction and an opposite rearward movement direction, in the forward movement direction the inspection apparatus moves in a direction towards the container, in the rearward movement direction the inspection apparatus moves in a direction away from the container, the inspection apparatus comprising;
a light detector for detecting light in the interior of the container;
a movable support having a first end, a second end and an inner through conduit extending between and through the first and second ends, the through conduit configured to communicate light received at the first end towards the light detector, the movable support movable between a first axial position and a second axial position, in the second axial position the second end of the movable support is located nearer the light detector than when the movable support is in the first axial position;
an elastic member that acts on the movable support to continuously urge the movable support towards the first axial position; and
a stop with an inner through opening located on the first end of the moveable support, the stop configured to contact the open end of the container in a manner that prevents light from entering the interior of the container through the open end of the container;
moving the light detector in the forward movement direction until the stop contacts the open end of the container;
activating the light detector after the stop contacts the open end of the container; and
continue moving the inspection apparatus in the forward movement direction to cause the moveable element to move from the first axial position towards the second axial position while continuing to activate the light detector.

16. The method according to claim 15, further comprising continuing to move the inspection apparatus in the forward movement direction until the movable support is in the second axial position while continuing to activate the light detector.

17. The method according to claim 16, further comprising moving the inspection apparatus in the rearward movement direction after the movable support is in the second axial position.

18. The method according to claim 17, wherein the light detector remains activated during at least a part of the rearward movement direction.

19. The method of claim 18 wherein the light detector is deactivated when the stop is not in contact with the open end of the container.

20. The method according to claim 17, wherein the light detector remains activated during only a part of the rearward movement direction.

21. The method according to claim 15, wherein a light source disposed about the outer surface of the container is activated when the stop comes into contact with the container, and is deactivated before the stop is no longer in contact with the container.

22. The method according to claim 15, wherein the light source is deactivated when the light detector detects light in the interior of the container.

* * * * *